United States Patent [19]

Abel, Jr.

[11] Patent Number: 4,810,082

[45] Date of Patent: Mar. 7, 1989

[54] CORNEAL ONLAY LENS

[76] Inventor: Robert Abel, Jr., 1100 N. Grant Ave., Wilmington, Del. 19805-2695

[21] Appl. No.: 68,359

[22] Filed: Jul. 1, 1987

[51] Int. Cl.⁴ .......................... G02C 7/04; A61F 2/14
[52] U.S. Cl. .......................... 351/160 R; 351/160 H; 623/5
[58] Field of Search .............. 351/160 R, 160 H, 161, 351/162; 623/4, 5

[56] References Cited

U.S. PATENT DOCUMENTS

| | | | |
|---|---|---|---|
| 2,754,520 | 7/1956 | Crawford | 351/160 R |
| 2,952,023 | 9/1960 | Rosen | 351/160 R |
| 3,074,407 | 1/1963 | Moon et al. | 351/160 R |
| 3,228,741 | 1/1966 | Becker | 351/160 R |
| 4,126,904 | 11/1978 | Shepard | 623/4 |
| 4,346,482 | 8/1982 | Tennant et al. | 623/4 |
| 4,466,705 | 8/1984 | Michelson | 350/418 |

Primary Examiner—John K. Corbin
Assistant Examiner—Scott J. Sugarman
Attorney, Agent, or Firm—Roylance, Abrams, Berdo & Goodman

[57] ABSTRACT

A device for correcting refractive errors in the eye comprising a synthetic corneal onlay lens. The lens has an annular projection received in an annular recess in the corneal outer surface and a mechanism for connecting the lens to the cornea. This mechanism comprises sutures received in throughbores in the lens and passing into the cornea, adhesive directly connecting the annular projection and the recess, or both. The annular projection and the recess can have conforming scalloped surfaces to increase the engaging surface areas, thereby reducing the chances of relative rotation and increasing the adhesion therebetween.

11 Claims, 3 Drawing Sheets

CORNEAL ONLAY LENS

FIELD OF THE INVENTION

The invention relates to devices for correcting refractive errors of the eye. More specifically, the invention relates to a synthetic corneal onlay lens received in an annular recess in the corneal outer surface and secured thereto.

DESCRIPTION OF THE PRIOR ART

The cornea and lens act in combination to focus light rays in the eye. Two prevalent vision problems, myopia (nearsightedness) and hyperopia (farsightedness), result from light rays not converging to a focal point precisely on the retina.

Myopic vision results when the light rays focus at a point anterior to the surface of the retina. That condition may be caused by the eyeball being axially too long or the cornea being too curved.

Hyperopic vision occurs when the light rays focus at a point posterior to the retina. That condition may be caused by the eyeball being axially too short or the cornea being too flat.

Contact lenses, adapted to fit over the cornea, refract light and therefore correct vision by varying the focal point of light rays entering the eye. Contact lenses can have different refractive indexes, i.e., prescriptions. Thus, by using the appropriate prescription, the focal point of the light rays can be moved to a position precisely on the retina.

Contact lenses are typically merely held by surface tension on the cornea. Such a lens, not being physically attached to the cornea, exhibits axial, rotational, and lateral movement relative to the surface of the cornea which affects vision. Attempts have been made to permanently attach a lens to the cornea, and thereby resist relative movement between the contact lens and the cornea. For example, see U.S. Pat. Nos. 3,228,741 to Becker; 4,126,904 to Shepard; 4,346,482 to Tennant et al.; and 4,466,705 to Michelson. However, such attempts have met with limited success because of one or more of the following drawbacks.

In Shepard, while an artificial lens is sutured to a cornea, there can still be relative movement between the lens and the cornea since the lens is flush with the corneal surface. In addition, Shepard requires haptics outside the optical part of the lens. In Tennant et al., while a living donor cornea has a ring received in a groove in a cornea and is temporarily sutured thereto, the host cornea may adversely react to the donor cornea. In addition, the donor cornea can become infected, is fragile and costly, and is hard to shape. In Becker and Michelson, there is no significant connection between an artificial lens and the host cornea, leading to possible relative movement therebetween.

SUMMARY OF THE INVENTION

Accordingly, it is an object of the invention to provide a synthetic corneal onlay lens permanently received in and secured to the cornea.

Another object of the invention is to provide a synthetic corneal onlay lens tightly secured to the cornea which does not exhibit any significant axial, rotational, or lateral movement relative to the cornea.

Another object of the invention is to provide a synthetic corneal onlay lens tightly secured to the cornea via permanent sutures, adhesive, or both.

Another object of the invention is to provide a synthetic corneal overlay lens secured to the cornea that does not adversely react with the patient's cornea, reduces the chances of infection, allows immediate return of vision and is relatively inexpensive to make.

The foregoing objects are basically obtained by a device for correcting refractive error in the eye and adapted to overlay the cornea, the combination comprising a synthetic lens having an anterior surface, a posterior surface, and a radially outwardly facing peripheral edge connecting the anterior and posterior surfaces; a posteriorly extending projection defined by the posterior surface and the peripheral edge, that projection being received in a recess formed in the outer surface of the cornea; and means coupled to the peripheral edge adapted to connect the lens to the cornea.

Other objects, advantages, and salient features of the present invention will become apparent from the following detailed description, which, taken in conjunction with the annexed drawings, discloses a preferred embodiment of the invention.

BRIEF DESCRIPTION OF THE DRAWINGS

Referring now to the drawings which form a part of this original disclosure.

DETAILED DESCRIPTION OF THE INVENTION

Figure 1:
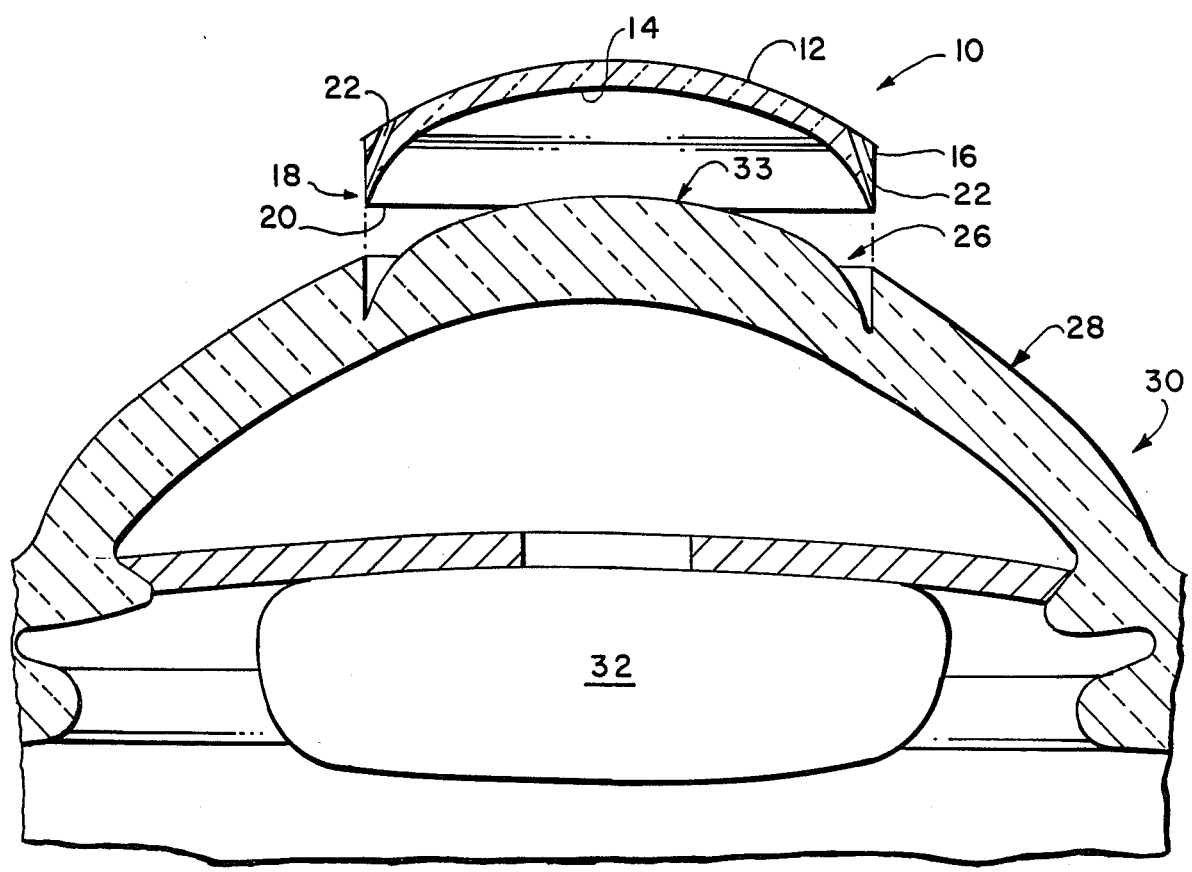
FIG. 1 is a cross-sectional elevational view of the corneal onlay lens in accordance with the invention together with a cornea having an annular recess formed in the outer surface thereof.
Figure 2:
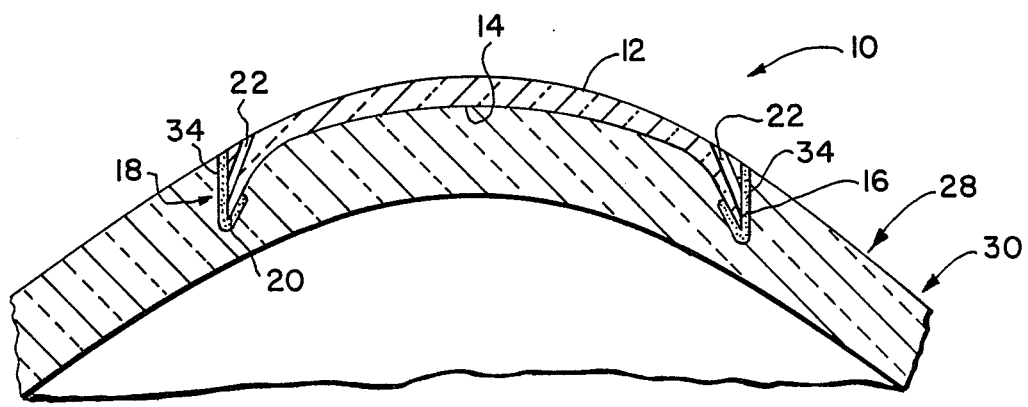
FIG. 2 is a cross-sectional elevational view of the corneal onlay lens and the cornea with the onlay lens received in the annular recess of the cornea.
Figure 3:
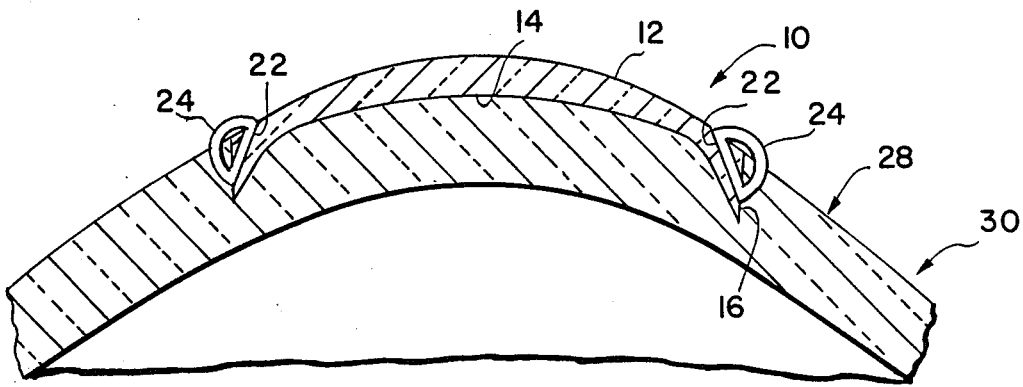
FIG. 3 is a cross-sectional elevational view of the corneal onlay lens received on the cornea and attached to the cornea by means of sutures, adhesive or both.
Figure 4:
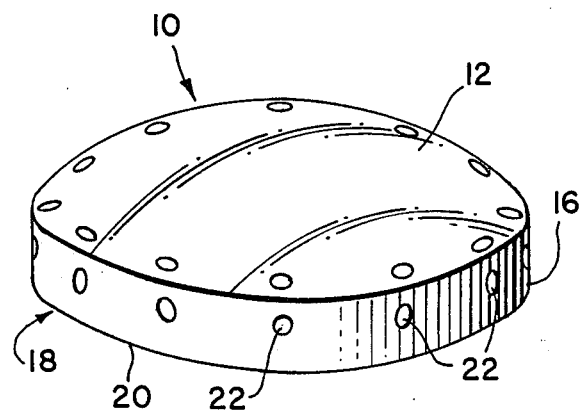
FIG. 4 is a perspective view of the corneal onlay lens shown in FIGS. 1-3.
Figure 5:
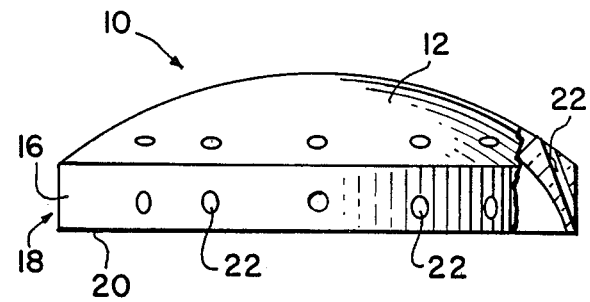
FIG. 5 is a side elevational view of the corneal onlay lens shown in FIGS. 1-4 with a portion in section.

As seen in FIGS. 1–3, a synthetic corneal onlay lens 10 in accordance with the invention is permanently received in and attached to a cornea 28 in an eye 30 having a natural lens 32.

The onlay lens 10 is substantially circular in plan view and comprises a convex anterior surface 12, a concave posterior surface 14, and a peripheral edge 16 connecting the anterior surface and the posterior surface. The peripheral edge is advantageously substantially cylindrical and is radially outwardly facing.

The thickness of the lens 10 between the anterior and posterior surfaces and the curvature of each of these surfaces can be varied to take into account the amount of refractive error being corrected.

The peripheral edge 16 and the concave posterior surface 14 intersect and form a posteriorly extending and inwardly tapering projection 18 having a circular distal edge 20 lying in a single plane. As seen in FIGS. 1–5, equally circumferentially spaced, substantially cylindrical throughbores 22 extend from the anterior surface 12 through the posterior projection 18 to the peripheral edge 16. The throughbores have a diameter sufficient to accommodate suturing thread 24 and advantageously number 8–24, with 12 being shown in FIGS. 1–5. The throughbores form acute angles with the longitudinal axis of the lens 10 and the overall optical axis of the eye 30.

The onlay lens 10 of this invention can be attached to the cornea 28 by using very simple surgical techniques. The method begins by removing a portion of the epithelium cells 33 on the outer surface of the cornea 28 in a central area which has a diameter of about 9 mm. This can be performed by, for example, a scalpel. Then the surgeon forms an annular recess 26 in the anterior portion of the cornea 28 conforming to the shape of the projection 18 on the lens as seen in FIG. 1 by using, for example, a trephine. Advantageously, the recess in the cornea extends beneath the epithelium layer and through the Bowman's membrane, since limited healing might be necessary. Then, the posteriorly extending projection 18 is placed fully into the recess and the posterior surface 14 engages the outer surface of the cornea. Finally, the onlay lens is sutured to the cornea via permanent sutures 24 received in the throughbores 22 and the cornea itself. The sutures are advantageously formed of polypropylene, a polyester fiber such as that sold under the trademark Mersilene by Ethicon, or stainless steel.

In addition to or in place of sutures 24, the onlay lens 10 can be secured to the cornea by use of an adhesive 34 interposed between projection 18 and the surface of the recess 26. The adhesive 34 is illustrated in FIG. 2, but omitted from FIGS. 1 and 3–5 for reasons of clarity. Such an adhesive is advantageously made from cyano acrylate fibrin, fibrin derivatives or plasma derivatives.

The onlay lens 10 comprises any hard or soft synthetic material that is (1) compatible with the patient's corneal tissue, (2) sufficiently rigid to prevent deformation by the pull of sutures, (3) resistant to degeneration, and (4) permeable to gases such as oxygen and carbon dioxide. The pore size, however, should be sufficiently small to prevent bacteria from entering the eye. Exemplary synthetic materials that can be used include methacrylates such as polymethyl methacrylate and hydroxyethyl methacrylate, silicone, siloxanes, styrenes, glass, lower alkyl butyrates, a silicone-acrylate copolymer, a fluorocarbon such as polytetrafluoroethylene, polypropylene, polyethylene terephthalate, Gore-Tex, which is a trademark for stretched polytetrafluoroethylene having approximately nine billion randomly spaced microscopic pores per square inch, each pore being 20,000 times smaller than a water droplet but 700 times larger than a water vapor molecule and is manufactured by W. L. Gore & Associates, 3 Blue Ball Road, Elkton, Md., or a combination of the above polymeric materials.

The onlay lens 10 can also include an ultraviolet chromophore to prevent degeneration of the lens from UV light and to protect the internal areas of the eye against UV toxicity.

Advantageously, the lens 10 has an outer diameter of from about 5 mm. to about 10 mm. Its thickness between the anterior and posterior surfaces is advantageously about 0.1 mm. to about 0.5 mm., with the maximum thickness occurring at the peripheral edge 16 or centrally thereof depending upon the refractive requirements and manufacturing techniques.

Figure 6:
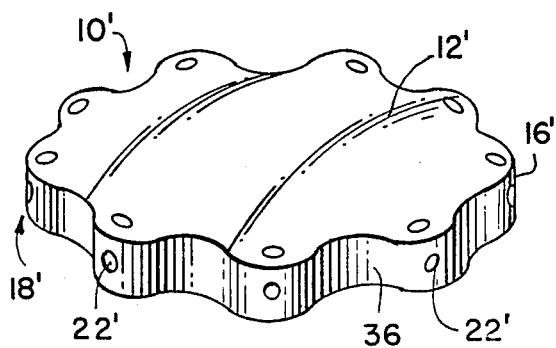
FIG. 6 is a perspective view illustrating a second embodiment of the invention characterized by the peripheral edge having periodic radially extending recesses therein.
Figure 7:
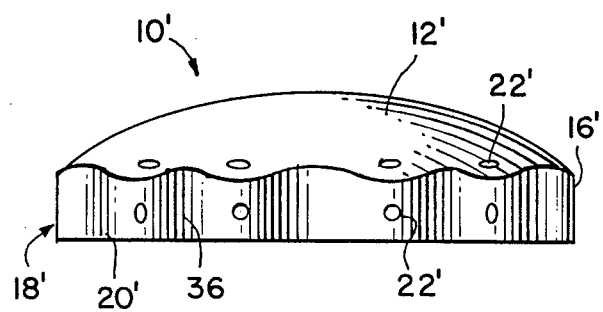
FIG. 7 is side elevational view of the embodiment shown in FIG. 6.

Embodiment of FIGS. 6–7

In FIGS. 6 and 7, a second embodiment of the onlay lens in accordance with the invention is shown and designated 10'. Lens 10' is similar to lens 10 except that the peripheral edge 16' undulates and has periodic radially extending scalloped recesses 36 of substantially the same depth and circumferential length. Thus, the edge 16' has a greater surface area to contact the radially inwardly facing part of the annular recess in the cornea, which would have corresponding periodic recesses. This provides a greater area for the adhesive 34 to couple the lens 10' to the cornea and also reduces the likelihood of the lens 10' rotating relative to the cornea. The remaining parts of lens 10' are the same as those of lens 10, although only eight throughbores are shown, and are given the same reference numerals with the addition of a prime.

Figure 8:
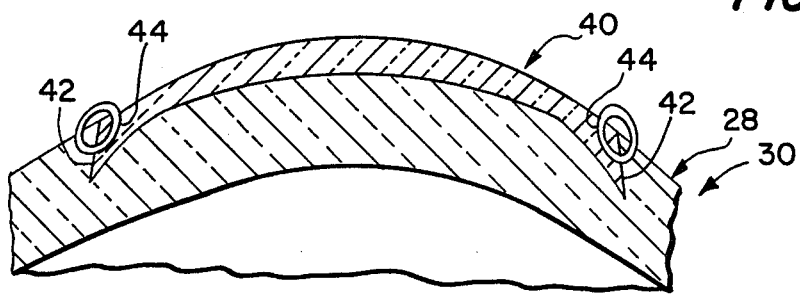
FIG. 8 is a cross-sectional elevational view of a third embodiment of the invention which is similar to the embodiment of FIGS. 1-4 except that the peripheral edge is upwardly and inwardly tapering.

Embodiment of FIG. 8

In FIG. 8, a third embodiment of the invention is shown in which lens 40 is similar to lens 10 shown in FIGS. 1–4 except that the peripheral edge 42 is frustoconical, i.e., upwardly and inwardly tapering, not cylindrical as in FIGS. 1–4. In addition, throughbores 44 are curved, not straight. The remaining structure is the same as that shown in FIGS. 1–4 and described above.

Figure 9:
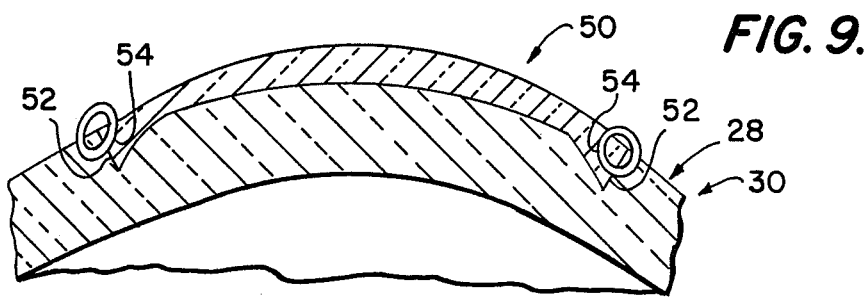
FIG. 9 is a cross-sectional elevational view of a fourth embodiment of the invention which is similar to the embodiment of FIGS. 1-4 except that the peripheral edge is downwardly and inwardly tapering.

Embodiment of FIG. 9

In FIG. 9, a fourth embodiment of the invention is shown in which lens 50 is similar to lens 10 shown in FIGS. 1–4 except that the peripheral edge 52 is frustoconical, not cylindrical as in FIGS. 1–4, and tapers downwardly and inwardly. In addition, throughbores 54 are curved, not straight. The remaining structure is the same as that shown in FIGS. 1–4 and described above.

Figure 10:
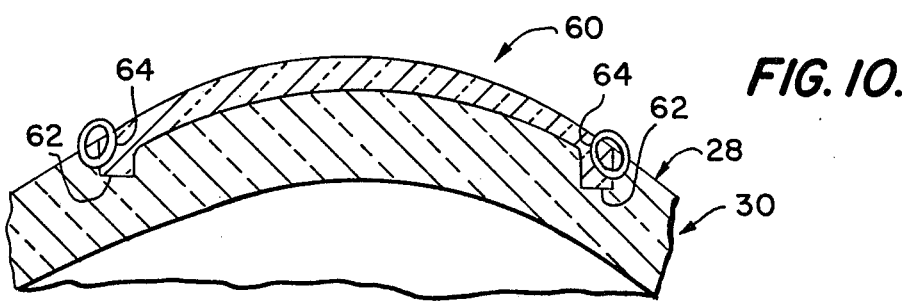
FIG. 10 is a cross-sectional elevational view of a fifth embodiment of the invention which is similar to the embodiment of FIGS. 1-4 except that the distal edge is in the form of a flat planar ring.

Embodiment of FIG. 10

In FIG. 10, a fifth embodiment of the invention is shown in which lens 60 is similar to lens 10 shown in FIGS. 1–4 except that the distal edge 62 has a radial thickness and is in the form of a flat planar ring. In addition, throughbores 64 are curved, not straight. The remaining structure is the same as that shown in FIGS. 1–4 and described above.

Figure 11:
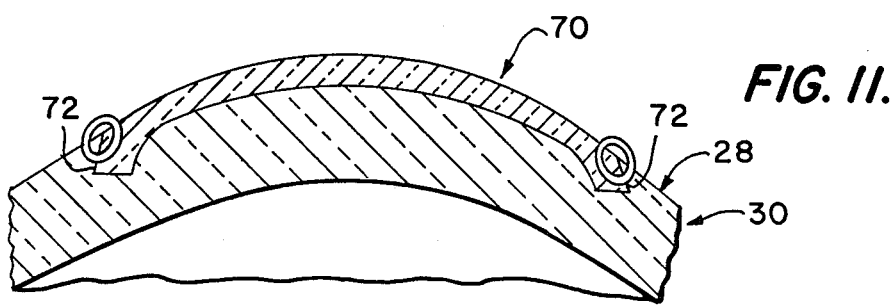
FIG. 11 is a cross-sectional elevational view of a sixth embodiment of the invention which is similar to the embodiment of FIG. 10 except that the peripheral edge is upwardly and inwardly tapering.

Embodiment of FIG. 11

In FIG. 11, a sixth embodiment of the invention is shown in which lens 70 is similar to lens 60 shown in FIG. 10 except that the peripheral edge 72 is a portion of a sphere and tapers upwardly and inwardly. The remaining structure is the same as that shown in FIG. 10 and described above.

While various advantageous embodiments have been chosen to illustrate the invention, it will be understood by those skilled in the art that various changes and modifications can be made therein without departing from the scope of the invention as defined in the appended claims.

What is claimed is:

1. A device for correcting refractive error in the eye and adapted to overlay a cornea, the combination comprising:
    a synthetic lens having an anterior surface, a posterior surface, and a radially outwardly facing peripheral edge connecting said surfaces;
    a posteriorly extending projection defined by said posterior surface and said peripheral edge, said projection being received in a recess formed in the outer surface of the cornea; and
    means for connecting said lens to the cornea including a plurality of throughbores extending from said anterior surface to said peripheral edge without penetrating said posterior surface, each of said throughbores having a diameter sufficient to accommodate suturing thread.

2. A device for correcting refractive error as defined in claim 1, wherein
    said plurality of throughbores comprises at least eight of said throughbores.

3. A device for correcting refractive error as defined in claim 1, wherein
    said peripheral edge has periodic recesses therein.

4. A device for correcting refractive error as defined in claim 1, wherein
    said lens comprises at least eight of said throughbores.

5. A device for correcting refractive error as defined in claim 1, wherein
    said means comprises sutures, said sutures being received in said throughbores and in the cornea.

6. A device for correcting refractive error as defined in claim 1, wherein
    said lens is formed of a polymeric material.

7. A device for correcting refractive error as defined in claim 6, wherein
    said polymeric material comprises silicone, siloxane, styrene, glass, polymethyl methacrylate, hydroxyethyl methacrylate, butyrate, a silicone-acrylate copolymer, a fluorocarbon, polypropylene, polyethylene terephthalate, stretched polytetrafluoroethylene having approximately nine billion randomly spaced microscopic pores per square inch, or a combination thereof.

8. A device for correcting refractive error as defined in claim 1, wherein
    said projection tapers inwardly in the posterior direction.

9. A device for correcting refractive error as defined in claim 1, wherein
    said peripheral edge is cylindrical.

10. A device for correcting refractive error as defined in claim 1, wherein
    said peripheral edge tapers.

11. A device for correcting refractive error as defined in claim 1, wherein
    said posteriorly extending projection has a flat, annular distal edge.

* * * * *